US008352408B2

(12) United States Patent
Guillama et al.

(10) Patent No.: US 8,352,408 B2
(45) Date of Patent: Jan. 8, 2013

(54) SYSTEM AND METHODS FOR PROVIDING INTEGRATED WELLNESS ASSESSMENT

(75) Inventors: Noel Guillama, Boca Raton, FL (US);
Pedro Martinez, Boca Raton, FL (US)

(73) Assignees: Quantum Group, Inc., Wellington, FL (US); Noel Guillama, Wellington, FL (US)

( * ) Notice: Subject to any disclaimer, the term of this patent is extended or adjusted under 35 U.S.C. 154(b) by 923 days.

(21) Appl. No.: 12/349,714

(22) Filed: Jan. 7, 2009

(65) Prior Publication Data
US 2009/0177613 A1 Jul. 9, 2009

Related U.S. Application Data

(60) Provisional application No. 61/019,524, filed on Jan. 7, 2008.

(51) Int. Cl.
*G06F 9/44* (2006.01)
*G06N 7/02* (2006.01)
*G06N 7/06* (2006.01)

(52) U.S. Cl. ........................................................ 706/52
(58) Field of Classification Search ........................ None
See application file for complete search history.

(56) References Cited

U.S. PATENT DOCUMENTS 5,937,387 A * 8/1999 Summerell et al. ............... 705/2
2006/0111944 A1 * 5/2006 Sirmans et al. .................... 705/3

OTHER PUBLICATIONS

'Elements of artificial neural networks': Mehrotra, 1997, MIT press.*

* cited by examiner

*Primary Examiner* — Kakali Chaki
*Assistant Examiner* — Peter Coughlan
(74) *Attorney, Agent, or Firm* — Novak Druce + Quigg LLP

(57) ABSTRACT

A system for generating measurable indexes for providing a total wellness assessment of an individual is provided. The system can include a communications interface for accessing databases of population data derived from samplings of populations. The system further can include an integration and synthesis engine for generating weighting factors based upon a combination of the data, each weighting factor corresponding to a body region of the individual or to a health condition associated with the individual and based upon the population data. The system also can include a conditions capture engine for capturing individual-specific data corresponding to predetermined health conditions. The system can further include a modeling tool for combining the weighting factors with the individual-specific data. Moreover, the system can include a quotient generator for generating an overall health score corresponding to the individual based on the combining of weighting factors, population data, and individual-specific data.

12 Claims, 2 Drawing Sheets

SYSTEM AND METHODS FOR PROVIDING INTEGRATED WELLNESS ASSESSMENT

CROSS-REFERENCE TO RELATED APPLICATIONS

This application claims the benefit of U.S. Provisional patent application No. 61/019,524, which was filed Jan. 7, 2008, and which is incorporated herein in its entirety.

FIELD OF THE INVENTION

The present invention is related to the fields of data analysis and processing, and more particularly, to analyzing and processing data derived from disparate sources so as to generate data-based indicia of an individual's overall health.

BACKGROUND OF THE INVENTION

A particular challenge in the fields of medicine and, indeed, healthcare generally is how to provide a quantitative assessment of an individual's overall health. Without some type of quantitative measurement, assessing the individual's current health and predicting his or her future health tends to varying degrees to be less precise. Conversely, a quantitative measurement of the individual's health can be useful to physicians and other healthcare providers in more rigorously evaluating the risks that an individual may yet develop a problematic medical condition in the future. Such a measurement, of course, is typically very helpful to insurance providers. Moreover, a quantitative measurement can convey to the individual himself or herself a more precise assessment of the individual's health condition, perhaps alerting the individual to change certain lifestyle or environmental variables so as to improve the individual's health.

Despite the benefits that a quantitative measurement of an individual's health can provide, conventional measurements tend to be limited to different, unrelated scores pertaining to distinct aspects of an individual's body and biological system. Accordingly, it is difficult to provide a total wellness assessment of an individual.

SUMMARY OF THE INVENTION

The present invention is directed to systems and methods for integrating health-relevant data from multiple sources and utilizing the integration to develop measurable indexes of an individual's wellness, or overall state of health. The systems and methods can incorporate and enhance statistically-valid sampling of various target populations.

One embodiment of the invention is a system for generating measurable indexes for providing a total wellness assessment of an individual. The system can include a data communications interface for accessing a plurality of databases of population data derived from samplings of one or more populations. Additionally, the system can include an integration and synthesis engine for generating a plurality of weighting factors based upon a predetermined combination of the data, each weighting factor corresponding to a predetermined body region of the individual or to a predetermined health condition associated with the individual and based upon the population data. The system also can include a conditions capture engine for capturing individual-specific data corresponding to a set of predetermined of health conditions associated with the individual. The system can further include a modeling tool for combining at least one of the plurality of weighting factors with the individual-specific data corresponding to a set of predetermined of health conditions associated with the individual. Moreover, the system can include a quotient generator for generating an individual-specific overall health score corresponding to the individual based on the combining of weighting factors, population data, and individual-specific data.

Another embodiment of the invention is a computer-implemented method for generating measurable indexes for providing a total wellness assessment of an individual. The method can include accessing a plurality of databases of population data derived from samplings of one or more populations; generating a plurality of weighting factors based upon a predetermined combination of the population data using a dynamic data integration and synthesis engine, each weighting factor corresponding to a predetermined body region of the individual or to a predetermined health condition associated with the individual and based upon the population data; and combining at least one of the plurality of weighting factors with individual-specific data corresponding to a set of predetermined of health conditions associated with the individual and based on the combining of weighting factors and individual-specific data computing an overall health score corresponding to the individual.

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

The invention is directed to systems and methods for synthesizing and integrating health-relevant data. One aspect of the invention is a system and related methods that synthesize and integrate such data so as to generate measurable indexes that, in context, provide more statistically valid samplings of population data and synthesize the data with individual- or patient-specific data to generate a total wellness assessment of an individual, including an evidence-based holistic measurement of an individual's health.

Figure 1:
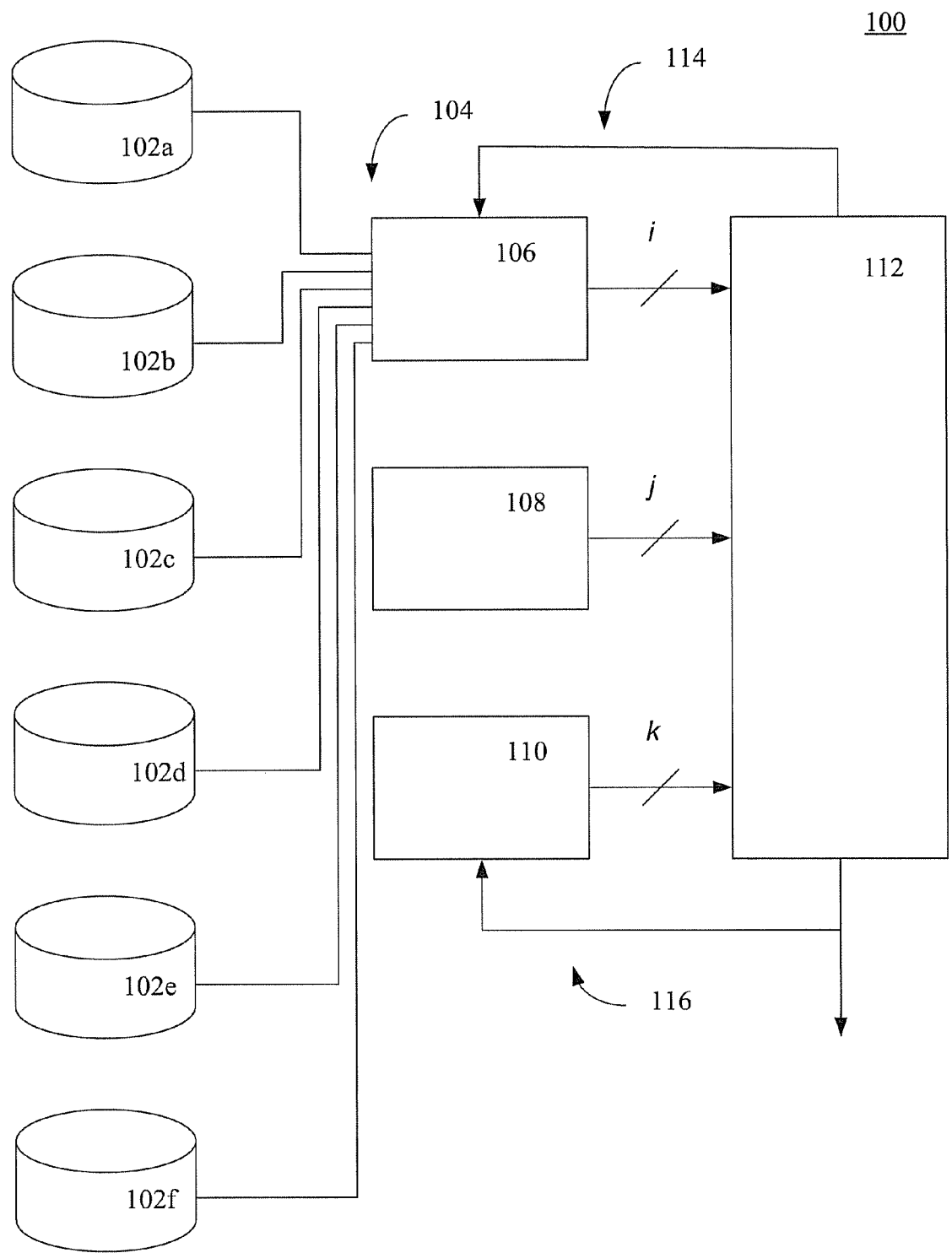
FIG. 1 is a schematic view of system for generating a total wellness assessment of an individual, according to one embodiment of the invention.

Referring initially to FIG. 1, a system 100 for generating measurable indexes for providing a total wellness assessment of an individual, according to one embodiment of the invention, is schematically illustrated. The system 100 illustratively includes a plurality of databases 202. Although an exemplary six databases 102*a-f* are shown, it will be readily apparent to one of ordinary skill based on the description herein that a different number of databases can be employed, be that number greater than or less than six.

The system 100 further illustratively includes a data communications interface 104. As shown, the interface 104 communicatively links each of the databases 102*a-f* with another element of the system 100. This element is termed an integration and synthesis engine 106, the operative features of which are described more particularly below. Additionally the system illustratively includes a conditions capture engine 108 and a modeling tool 110. Both the conditions capture engine 108 and the modeling tool 110 are communicatively linked to a quotient generator 112. The integration and synthesis engine likewise is communicatively linked to the quotient generator.

The databases 102a-f can communicatively link to the integration and synthesis engine 106 through the data communications interface 104 directly, as illustrated. In an alternate embodiment, however, the databases 102a-f can communicatively link to the integration and synthesis engine 106 through a data communications network (not explicitly shown). The network can be a local-area network (LAN), wide-area network (WAN), or the Internet. Thus, in any of these alternative embodiments the data communications interface 104 can be appropriately configured to communicatively link to one or more such data communications network.

One or more of the integration and synthesis engine 106, conditions capture engine 108, the modeling tool 110, and quotient generator 112 can be implemented in hardwired, dedicated circuitry for performing the operative functions described herein. Alternatively, however, one or more of these elements of the system 100 can be implemented in computer-readable code. Accordingly, the integration and synthesis engine 106, conditions capture engine 108, the modeling tool 110, and/or quotient generator 112 can be implemented in computer-readable code configured to execute on a general-purpose or application-specific computing device. In still another embodiment, however, one or more of these system elements can be implemented in a combination of hardwired circuitry and computer-readable code.

Operatively, the data communications interface 104 accesses the plurality of databases 102a-f. The different databases 102a-f store population data derived from samplings of one or more populations. As already noted, the number of databases of the system 100 can vary. Accordingly, the depth and breadth of the population data also can vary accordingly. The databases provide statistically valid samples of respective populations, as will be readily understood by one of ordinary skill in the art.

For example, the databases 102a-f can include demographic data, including regional statistics, job types, gender-relevant data, age-relevant data, environmental conditions, and any of a host of other data pertinent to assessing the health of representatives of the corresponding population. Additionally, the databases 102a-f can include an historical information database, which provides a timeline of information for tracing health statistics, such as the origins and trends of diseases, relevant treatments and medicines. Such data can include or be correlated with environmental and demographic groupings to disclose interactions between health of a population and environmental and/or demographic factors. The databases 102a-f also can include an actuarial database, which integrates insurance-related information such as risk probabilities and statistical assessments. Another of the databases 102a-f can be a medical database containing medical information extracted from a variety of sources pertaining to diseases, treatments, forms of "best practices" for health, and other medical information. The databases 102a-f also can include a genomic database that perhaps provides the most enhanced insight into the functioning of the human body; it can provide context linking genetic code to various physical, environmental, and behavioral factors of the representative population. Accordingly, this later database can provide insights into conditions and treatments in a dynamic and predictive manner.

Operatively, the integration and synthesis engine 106 generates a plurality of weighting factors based upon a predetermined combination of the population data, each weighting factor corresponding to a predetermined body region of the individual or to a predetermined health condition associated with the individual and based upon the population data. As illustrated, a variable number of data inputs can be supplied through the data communications interface 104 from the databases 102a-f to the integration and synthesis engine 106. Representative of such data is data relevant to age, sex, weight, blood pressure, cholesterol, smoking, job and profession, blood sugar, geography, and environmental factors, all of which can be used to derive the weighting factors based upon valid statistical techniques. The statistics can be based on relevant and emerging diseases, which one can monitor and which are modeled in the context of specific individuals as described herein. Similarly, established and measurable treatments can be factored into the model in order to determine direct health implications of these various factors.

The integration and synthesis engine 106 can be configured to compute and synthesize the disparate information drawn from the databases 102a-f. The integration and synthesis engine 106 thus can combine information from various sources with different perspectives and assign weighting factors to different health and biological elements. In this way health trends can be more readily discerned. For example, identifying an increasing prevalence of diabetes can indicate that a person's weight is a more significant factor, on average, than the person's cholesterol level in predicting long-term health of the individual. These weighting factors can be graduated by the integration and synthesis engine 106.

The conditions capture engine 108 operatively functions by capturing individual-specific data corresponding to a set of predetermined of health conditions associated with the individual. More particularly, the conditions capture engine 108 can capture current, historical, and genomic information pertaining to a specific individual and overlay the information with relevant weighting factors generated by the integration and synthesis engine 106.

At this point, the modeling tool 110 is configured to combine one or more of the plurality of weighting factors with the individual-specific data corresponding to a set of predetermined health conditions associated with the individual. The modeling tool projects or forecasts the impact that certain aspects of the individual body condition, behavioral attributes, environment, or other individual specific factors has on the individual's overall health score. For example, a person with a good diet and exercise regime may yet exhibit high levels of cholesterol. The individual's genomic profile and historical information may highlight this as a genetic trait. Accordingly, a stricter diet and more exercise is likely to have only minimal effect in reducing the individual's level of cholesterol, but targeted medications may provide immediate benefits.

Operatively, the quotient generator 112 generates an individual-specific overall health score corresponding to the individual based on the combining of weighting factors, population data, and individual-specific data. That is, the quotient generator 112 combines i units of information generated by the integration and synthesis engine 106 with j units of information generated by the conditions capture engine 108 and with k units of information generated by the modeling tool 110. By synthesizing the disparate data, the system 100 is able to create a numerical value of the individual's health.

For example, population data derived from the databases 102a-f can include data corresponding to the variables AGE, SEX, WEIGHT, BLOOD PRESSURE, and CHOLESTEROL that is supplied by the integration and synthesis engine 106 to the quotient generator 112. The data can be overlaid with individual-specific data of 55 YEARS, MALE, 120 LBS., 130/90, and 234, corresponding to each of the exemplary population variables, which is supplied by the conditions capture engine 108. The modeling tool 110 can model various types of information so as to add new variables or data for projecting how an individual's health score would be altered by changes in health, behavioral, and/or environmental conditions. As already described, the quotient generator 112 can synthesize this disparate data to generate an overall wellness score for the individual.

Optionally, the system 100 can include one or more feedback mechanisms 114, 116. Accordingly, the system 100 is able to implement a dynamic model that can be refined based on various learning system principles, such as neural networks, machine learning, and the like. The system 100, accordingly, can be characterized as a closed-loop system.

The following statistical calculations can be employed. A first equation provides one population measure of wellness, termed here a quantum quotient, Q:

$$Q = \sum_{i=0}^{n} \frac{[(f_{1i} \cdot x_{1i}) + (f_{2i} \cdot x_{2i}) \ldots (f_{mi} \cdot x_{mi})]}{n},$$

where $f_{ji}$ is a weighting factor of individual i-th and the j-th of the m factors, which can include, for example, the following health-related factors: age, sex, weight, blood pressure, and blood sugar level for the i-th individual. For an individual, a quantum quotient, Q can similarly be computed:

$$Q = \frac{(f_1 \cdot x_1) + (f_2 \cdot x_2) \ldots (f_m \cdot x_m)}{m},$$

where, again, $f_j$ is a weighting factor applied to the j-th of the m factors, which can also include, for example, age, sex, weight, blood pressure, and blood sugar level. With an additional equation, positive or negative deviations can be factored against an established norm to create statistically-valid integrated scores:

$$Q' = \sum_{i=0}^{n} \frac{[(f_{1i} \cdot x_{1i} \pm \mu_{1i}) + (f_{2i} \cdot x_{2i} \pm \mu_{2i}) \ldots (f_{mi} \cdot x_{mi} \pm \mu_{mi})]}{n}.$$

Figure 2:
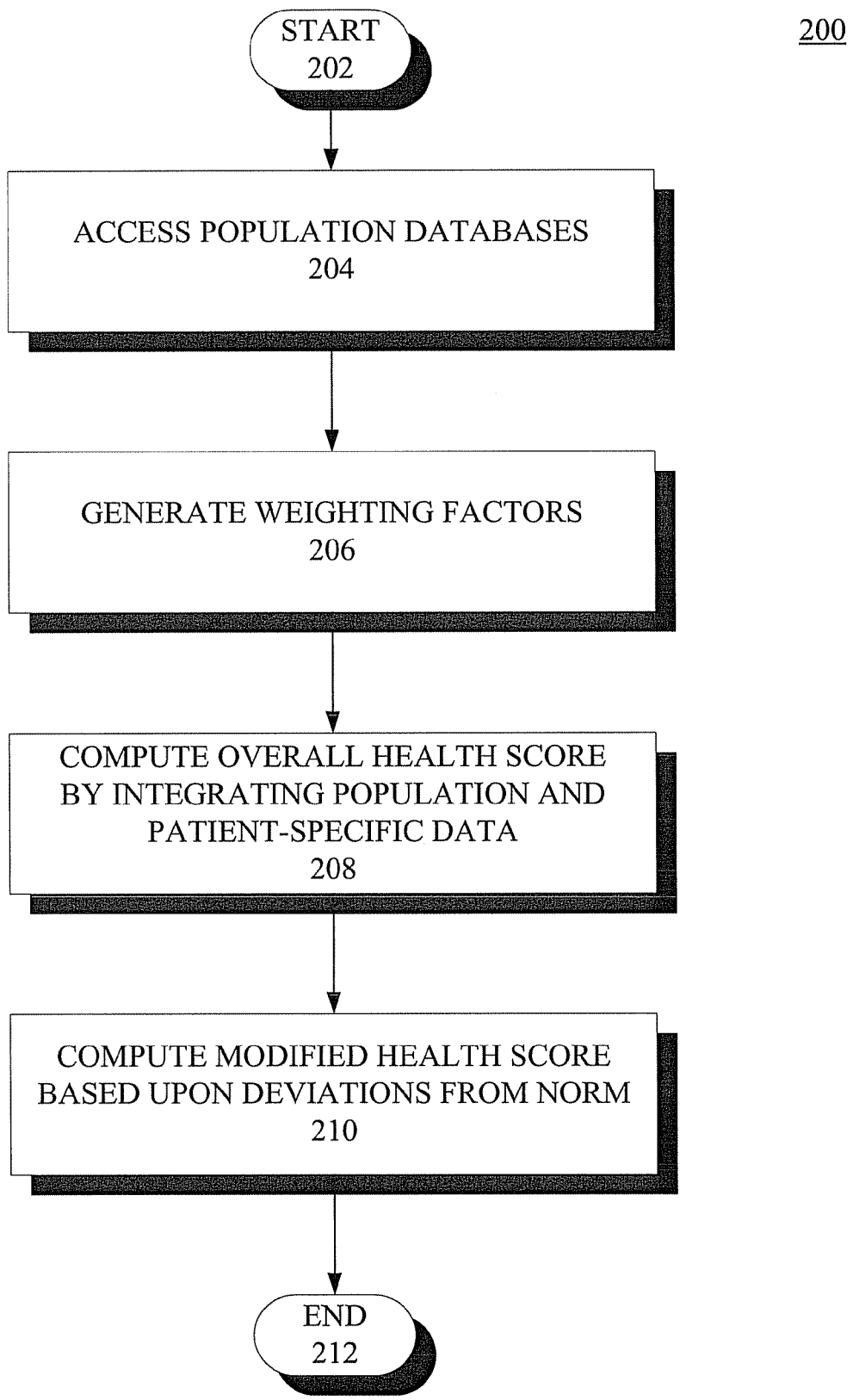
FIG. 2 is a flowchart of exemplary steps in a method for generating a total wellness assessment of an individual, according to another embodiment of the invention.

Referring now to FIG. 2, a flowchart is provided that illustrates certain method aspects of the invention. The flowchart depicts exemplary steps of a method 200 for generating measurable indexes for providing a total wellness assessment of an individual, according to another embodiment of the invention. The method illustratively includes, after the initial step 202, accessing a plurality of databases of population data derived from samplings of one or more populations at step 204. The method 200 additionally includes generating at step 206 a plurality of weighting factors based upon a predetermined combination of the population data using a dynamic data integration and synthesis engine. Each weighting factor, more particularly, corresponds to a predetermined body region of the individual or to a predetermined health condition associated with the individual and based upon the population data The method 200 also includes combining at least one of the plurality of weighting factors with individual-specific data corresponding to a set of predetermined of health conditions associated with the individual and, based on the combining of weighting factors and individual-specific data, computing an overall health score corresponding to the individual at step 208.

The method 200 optionally can also include computing an integrated overall health score, as shown by optional step 210. The integrated overall health score can be based upon at least one deviation between the overall health score and a statistical norm derived from population data contained in one or more of the plurality of databases. The method 200 illustratively concludes at step 212.

More particularly, computing the integrated overall health score can be based upon projected changes in predetermined health conditions associated with the individual. Computing the integrated overall health score can be based upon projected environmental changes affected the individual.

According to another embodiment, the method 200 can further include generating a list of recommendations for the individual based upon the projected changes. The list of recommendations, more particularly, can include a therapeutic regime for the individual, an environmental change, and/or a behavioral change.

The method 200, according to yet another embodiment, can include updating at least one of the weighting factors. The updating can be based upon a statistically estimated trend.

The invention, as already noted, can be realized in hardware, software, or a combination of hardware and software. The invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention, as also already noted, can be embedded in a computer program product, such as a computer-readable storage medium or device which when loaded in a computer system is able to carry out the different methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The foregoing description of preferred embodiments of the invention have been presented for the purposes of illustration. The description is not intended to limit the invention to the precise forms disclosed. Indeed, modifications and variations will be readily apparent from the foregoing description. Accordingly, it is intended that the scope of the invention not be limited by the detailed description provided herein.

We claim:

1. A computer-implemented method for generating measurable indexes for providing a total wellness assessment of an individual, the method comprising:

accessing a plurality of databases of population data derived from samplings of one or more populations the population data comprising data regarding a plurality of health related factors for the one or more populations;

generating a plurality of weighting factors based upon a predetermined combination of the population data using a dynamic data integration and synthesis engine, each of the plurality of weighting factors corresponding to a different one of the plurality of health related factors;

computing an first overall health score corresponding to the individual by combining at least one of the plurality of weighting factors with individual-specific data corresponding to at least a portion of the health related factors associated with the individual;

computing an second overall health score corresponding to the one or more populations by combining the at least one of the plurality weighting factors with individual specific data corresponding to the portion of the health related factors associated with individuals in the one or more populations;

determining a wellness of the individual related to the one or more populations based on the first and second overall health scores;

deriving one or more sets of deviations for the plurality of health related factors the sets of deviations based upon projected changes in at least one therapeutic regime, environment, or behavior associated with the individual; and recalculating the first overall health scores for the individual using each of the sets of deviations to yield integrated overall health scores for each of the sets of deviations.

2. The method of claim 1, further comprising generating a list of recommendations for the individual based upon the projected changes, the list of recommendations comprising at least one therapeutic regime, an environmental change, or a behavioral change.

3. The method of claim 1, wherein the plurality of database comprise at least one of a demographic database, an historical database, an actuarial database, a medical database, and a genomic database; and wherein the step of accessing comprises retrieving at least one of demographic data from the demographic database, historical data from the historical database, actuarial data from the actuarial database, medical data from the medical database, and genomic data from the genomic database.

4. The method of claim 1, further comprising updating at least one of the weighting factors based upon a statistically estimated trend.

5. A system for generating measurable indexes for providing a total wellness assessment of an individual, the system comprising:

a processor;

a data communications interface for accessing a plurality of databases of population data derived from samplings of one or more populations the population data comprising data regarding a plurality of health related factors for the one or more populations; and a computer readable medium have stored thereon instructions for causing the processor to perform steps comprising:

generating a plurality of weighting factors based upon a predetermined combination of the data, each of the plurality of weighting factor corresponding to a different one of the plurality of health related factors, capturing individual-specific data corresponding to at least a portion of the health related factors associated with the individual, computing an first overall health score corresponding to the individual by combining at least one of the plurality of weighting factors with the individual-specific data corresponding to a set of predetermined of health conditions associated with the individual, computing an second overall health score corresponding to the one or more populations by combining the at least one of the plurality weighting factors with individual specific data corresponding to the portion of the health related factors associated with individuals in the one or more populations, and determining a wellness of the individual related to the one or more populations based on the first and second overall health scores, deriving one or more sets of deviations for the plurality of health-related factors the sets of deviations based upon projected changes in at least one of therapeutic regime, environment, or behavior associated with the individual and recalculating the first overall health scores for the individual using each of the sets of deviations to yield integrated overall health scores for each of the sets of deviations.

6. The system of claim 5, the steps further comprising generating a list of recommendations for the individual based upon the projected changes, the list of recommendations comprising at least one therapeutic regime, an environmental change, or a behavioral change.

7. The system of claim 5, wherein the plurality of databases comprise at least one of a demographic database, an historical database, an actuarial database, a medical database, and a genomic database; and wherein the step of accessing comprises retrieving at least one of demographic data from the demographic database, historical data from the historical database, actuarial data from the actuarial database, medical data from the medical database, and genomic data from the genomic database.

8. The system of claim 5, wherein the integration and synthesis engine Is further configured to update at least one of the weighting factors based upon a statistically estimated trend.

9. A non-transitory computer-readable storage medium having computer-readable code embedded therein, which, when loaded in and executed by a computing device, causes the computing device to perform the steps of:

accessing a plurality of databases of population data derived from samplings of one or more populations the population data comprises data regarding a plurality of health related factors for the one or more populations;

generating a plurality of weighting factors based upon a predetermined combination of the data using a dynamic data integration and synthesis engine, each of the plurality of weighting factors corresponding to a different one of the plurality of health related factors;

computing an first overall health score corresponding to the individual by combining at least one of the plurality of weighting factors with individual-specific data corresponding to at least a portion of the health related factors associated with the individual;

computing an second overall health score corresponding to the one or more populations by combining the at least one of the plurality weighting factors with individual specific data corresponding to the portion of the health related factors associated with individuals in the one or more populations;

determining a wellness of the individual related to the one or more populations based on the first and second overall health scores;

deriving one or more sets of deviations for the plurality of health related factors the sets of deviations based upon projected changes in at least one therapeutic regime, environment or behavior associated with the individual; and recalculating the first overall health scores for the individual using each of the sets of deviations to yield integrated overall health scores for each of the sets of deviations.

10. The non-transitory computer readable medium of claim 9, further comprising code for causing the computer device to generate a list of recommendations for the individual based upon the projected changes, the list of recommendations comprising at least one therapeutic regime, an environmental change, or a behavioral change.

11. The non-transitory computer-readable storage medium of claim 9, wherein the plurality of databases comprise at least one of a demographic database, an historical database, an actuarial database, a medical database, and a genomic database; and wherein the step of accessing comprises retrieving at least one of demographic data from the demographic database, historical data from the historical database, actuarial data from the actuarial database, medical data from the medical database, and genomic data from the genomic database.

12. The non-transitory computer-readable of claim 9, further comprising code for causing the computing device to update at least one of the weighting factors based upon a statistically estimated trend.

* * * * *